United States Patent
Li et al.

(10) Patent No.: US 8,646,246 B2
(45) Date of Patent: Feb. 11, 2014

(54) METHOD OF PREPARING A COMPOSITION IN BLISTER PACKAGES

(75) Inventors: Hewei Li, Beijing (CN); Congwei Wang, Beijing (CN); Bo Du, Beijing (CN); Chenggong Jia, Beijing (CN); Shirong Jiao, Beijing (CN); Chun Ji, Beijing (CN)

(73) Assignee: Quantum Hi-Tech (Beijing) Research Institute, Beijing (CN)

( * ) Notice: Subject to any disclaimer, the term of this patent is extended or adjusted under 35 U.S.C. 154(b) by 109 days.

(21) Appl. No.: 12/142,506

(22) Filed: Jun. 19, 2008

(65) Prior Publication Data

US 2008/0305289 A1 Dec. 11, 2008

Related U.S. Application Data

(63) Continuation-in-part of application No. PCT/CN2006/003487, filed on Dec. 19, 2006.

(30) Foreign Application Priority Data

Dec. 19, 2005 (CN) .......................... 2005 1 0129999

(51) Int. Cl.
*B65B 55/14* (2006.01)
(52) U.S. Cl.
USPC ................................ 53/440; 53/454; 53/560
(58) Field of Classification Search
USPC ........... 43/440, 453, 433, 454, 514, 127, 560; 53/440, 453, 433, 454, 514, 127, 560
See application file for complete search history.

(56) References Cited

U.S. PATENT DOCUMENTS

| | | | | |
|---|---|---|---|---|
| 3,892,058 A | * | 7/1975 | Komatsu et al. | 53/425 |
| 4,096,309 A | * | 6/1978 | Stillman | 442/382 |
| 4,214,029 A | * | 7/1980 | Barnes | 428/200 |
| 4,223,512 A | * | 9/1980 | Buchner | 53/425 |
| 4,268,531 A | * | 5/1981 | Whiting, Jr. | 426/126 |
| 4,278,716 A | * | 7/1981 | Buchner et al. | 428/35.8 |
| 4,305,502 A | * | 12/1981 | Gregory et al. | 206/532 |
| 4,309,466 A | * | 1/1982 | Stillman | 428/35.3 |
| 4,310,578 A | * | 1/1982 | Katsura et al. | 383/108 |
| 5,343,672 A | * | 9/1994 | Kearney et al. | 53/440 |
| 5,729,958 A | * | 3/1998 | Kearney et al. | 53/440 |
| 6,337,113 B1 | | 1/2002 | Muggli et al. | |

FOREIGN PATENT DOCUMENTS

| | | |
|---|---|---|
| CN | 1089829 A | 7/1994 |
| CN | 1597310 A | 3/2005 |
| EP | 1488921 A1 | 12/2004 |

OTHER PUBLICATIONS

International Search Report for International Application No. PCT/CN2006/003487 dated Mar. 29, 2007, 3 pages.
European Search Report for European Application No. 06828395.1 dated Mar. 7, 2013, 7 pages.

* cited by examiner

*Primary Examiner* — Sameh H. Tawfik
(74) *Attorney, Agent, or Firm* — Jun He Law Offices P.C.; Zhaohui Wang

(57) ABSTRACT

The present invention provides methods for preparing compositions in blister packages using complex aluminum substrate materials, wherein said complex aluminum substrate materials comprise an intermediate aluminum layer, and first and second outer layers, wherein the material of the first outer layer differs from that of the second outer layer, and the flexural rigidity of the first outer layer differs from that of the second outer layer by 0-30%.

11 Claims, 1 Drawing Sheet

METHOD OF PREPARING A COMPOSITION IN BLISTER PACKAGES

CROSS REFERENCE TO RELATED APPLICATIONS

This is a continuation-in-part application of International PCT Application No. PCT/CN2006/003487 filed on Dec. 19, 2006, which claims priority to Chinese Patent Application No. 200510129999.0 filed on Dec. 19, 2005, each of which is incorporated herein by reference in its entirety.

FIELD OF THE INVENTION

This invention is related to methods of preparing pharmaceuticals and other materials in blister packages comprising complex aluminum package materials.

BACKGROUND OF THE INVENTION

At present, single-dose oral preparations are primarily packed in aluminum-plastic blister packages in the pharmaceutical area. Such packages have many advantages. First, it provides single-dose pharmaceutical packages for patients that are quite convenient and economical and avoids over dosage or insufficient dosage by patients. Second, blister package production is fast with low cost, takes up less storage space and is convenient to transport. Lastly, it is safe because the surface of the aluminum foil contains explanatory notes, which can help avoid mistakes during drug distribution when multiple drugs are distributed. Therefore, oral preparations with blister packages will dominate the market for a period of time in the future. However, the polymer materials used in blister packages, by their own properties, cannot prevent light and moisture from permeating the packages or contacting the pharmaceuticals contained therein, and thus affect the quality of the pharmaceuticals. To solve this problem, double aluminum layer packages, wherein the blister packages contain complex aluminum materials having polymer materials attached to the top and bottom of the aluminum foil, were used. The strong blocking property of the aluminum foil prevents the pharmaceuticals from damages brought about by outside factors such as light, moisture, bacteria, etc. and therefore extends the storage life of the products. This kind of package is important to pharmaceuticals that are vulnerable to effects from the outside environment, especially to the oral disintegrating preparations. If the oral disintegrating preparations are exposed to the moisture in the air, they may shrink substantially, which will prolong the disintegrating time and result in the products' failure to meet the quality requirements.

In addition, an oral disintegrating preparation can rapidly disintegrate in the mouth when it contacts the saliva without the need of water to wash it down, which is convenient to patients who have swallowing problems or cannot access water. More and more patients appreciate its unique advantages. Meanwhile, as the research has deepened, it has been discovered that besides its easy administration, this kind of preparation can be absorbed through mouth, throat and esophagus mucous membranes and thus takes effect quickly. Therefore, it can be used to develop pharmaceuticals for treating acute diseases such as pain diseases, insomnia, vomit, epilepsy, allergic and heart diseases, etc. The preparation can reduce the first pass effect of the liver, enhance medicine utility, reduce toxicity, and so on. It also has a great market prospect and has become the hotspot for research and development in the new formulation area and thus has attracted great attention.

Methods of manufacturing oral disintegrating preparations mainly include the direct compression process and the freeze-drying method. Tablets manufactured using the direct compression process have the biggest carrying capacity, the lowest cost and the widest application range. But the molding of the tablets and the time required for disintegration are contradictory to each other. In other words, the more pressure the compression has, the better the tablets will be molded, but this will prolong the disintegrating time. On the other hand, in order to ensure faster disintegrating speed, the tablets will be loose and may be worn down or even broken in the process of packing, storage and transportation.

In order to solve the problems concerning the direct compression process, oral disintegrating tablets manufactured with the freeze-drying method appeared in the market, for example, the Zydis technology. But using this technology leads to other problems. Because pharmaceuticals together with complex package materials are molded and rapidly frozen in ultra low temperature during the manufacturing process, the substrate materials of the package materials warp after the freeze-drying and affect the subsequent process. For example, it will have adverse effects on the sealing process and decrease the product quality. To solve these problems, CN 93121709.1 published a method of manufacturing oral disintegrating preparations using complex aluminum as substrate materials in the freeze-drying method by which the thermal expansion coefficients of the first and second outer layers of the substrate materials of the package must be the same. In this published document, the principle of requiring the same thermal expansion coefficients of the substrate materials is that, when the substrate materials are subject to the temperature changes in the process of freeze-drying, the first outer layer and the second outer layer must respond symmetrically to the temperature changes in order to prevent the substrate materials from warping after freeze-drying. The first and the second outer layers of the substrate materials must have the same thermal expansion coefficients so as to have symmetrical reaction to the temperature changes.

But the inventors of this invention discovered in their studies that during the aforesaid manufacturing process, the reason that the substrate materials warp before sealing the pharmaceuticals with lidding materials is that they are affected by the joint effects of two processes, namely, the aluminum depression molding process of the substrate materials and the freeze-drying process after filling in the pharmaceuticals. Meanwhile, the inventors of this invention further discovered through numerous experimentations that although the warp of the substrate materials is affected by the aforesaid two processes, the molding process exercises the most influence. Although the freeze-drying process also has influence on the warp of the substrate materials, its effect is negligible when compared with that of the molding process. This indicates that as long as the substrate materials do not warp after the molding process, it will satisfy the technical requirements even if it warps a little in the process of freeze-drying. After a long time of research and experimentation, the inventors of this invention finally discovered the technical solution to this question, and thus have accomplished this invention.

SUMMARY OF THE INVENTION

The present invention provides a method for manufacturing a composition in blister packages, comprising: (a) molding a complex aluminum substrate material with blister molding equipment, forming a plurality of depressions in said complex aluminum substrate material, wherein said complex aluminum substrate material comprises an intermediate aluminum layer, and first and second outer layers, wherein the material of the first outer layer differs from that of the second outer layer, and the flexural rigidity of the first outer layer differs from that of the second outer layer by 0-30%; (b) filling a liquid composition into the depressions formed in step (a); (c) freezing the composition; (d) freeze-drying the composition; (e) attaching a lidding material to said package material to seal the composition.

DETAILED DESCRIPTION OF THE INVENTION

Figure 1:
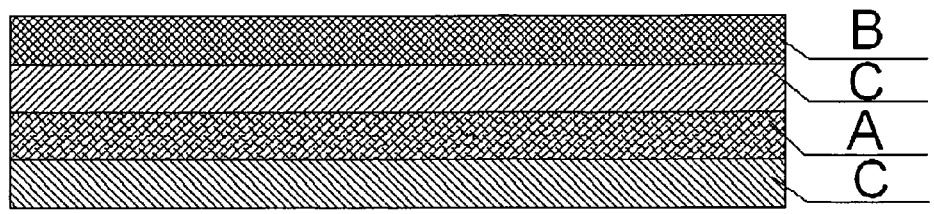
FIG. 1 is a structural diagram of a four-layer complex aluminum material used in a preferred embodiment of this invention. A stands for an aluminum foil layer, B stands for a water-based PE layer, and C stands for an OPA layer.

The present invention provides methods for preparing compositions in blister packages composed of complex aluminum package materials. Compositions that may be prepared in the blister packages include pharmaceuticals, cosmetics, nutritional supplements, food, seasonings, and any other materials of interest. Preferably, the compositions are pharmaceuticals, especially oral disintegrating preparations. The compositions may be in liquid or solid form. Preferably, the compositions are suitable for freeze drying.

In one aspect of the present invention, the blister packages are composed of complex aluminum package materials comprising of multiple layers of materials. The materials of different layers may have different physical and/or chemical properties. Each layer may have multiple sub-layers, wherein the sub-layers may have different physical and/or chemical properties.

In another aspect of the present invention, the blister packages are composed of complex aluminum package materials comprising of an intermediate aluminum layer, a first outer layer on one side of the aluminum layer, and a second outer layer on the other side of the aluminum layer. The first and second outer layers may be composed of different materials. The materials of the first and second outer layers may have different physical and/or chemical properties. For example, the first and second outer layers may be different chemical materials; the first and second outer layers may have different linear, area or volumetric thermal expansion coefficients; the first and second outer layers may have different thicknesses; the first and second outer layers may have different flexural rigidity values. The first and second outer layers may each have multiple sub-layers of different materials with different physical and/or chemical properties.

In one aspect, the present invention provides a method for manufacturing a composition in blister packages, comprising:

(a) molding a complex aluminum substrate material with blister molding equipment, forming a plurality of depressions in said complex aluminum substrate material, wherein said complex aluminum substrate material comprises an intermediate aluminum layer, and first and second outer layers, wherein the material of the first outer layer differs from that of the second outer layer, and the flexural rigidity of the first outer layer differs from that of the second outer layer by 0-30%;

(b) filling a liquid composition into the depressions formed in step (a);

(c) freezing the composition;

(d) freeze-drying the composition;

(e) attaching a lidding material to said package material to seal the composition.

In another aspect, the present invention provides a method for manufacturing an oral disintegrating preparation, comprising:

(a) molding a complex aluminum substrate material with blister molding equipment, forming a plurality of depressions in said complex aluminum substrate material, wherein said complex aluminum substrate material comprises an intermediate aluminum layer, and first and second outer layers, wherein the material of the first outer layer differs from that of the second outer layer, and the flexural rigidity of the first outer layer differs from that of the second outer layer by 0-30%;

(b) filling liquid pharmaceuticals into the depressions formed in step (a);

(c) freezing the pharmaceuticals;

(d) freeze-drying the pharmaceuticals;

(e) attaching a lidding material to said package material to seal the pharmaceuticals.

In the present invention, the material of the first outer layer may differ from that of the second outer layer, and the flexural rigidity of the first outer layer may differ from that of the second outer layer by no more than 30%. In certain embodiments, the difference in the flexural rigidity of the first outer layer and the second outer layer may be 0-30%. Furthermore, depending on the requirements of the technology, the difference in the flexural rigidity is preferably 0-15%, and more preferably 0-5%, and most preferably, the flexural rigidity of the first and second outer layers is the same. However, the present invention does not require that the thermal expansion coefficient of the first outer layer and the second outer layer be the same.

In a preferred embodiment, at least one layer of the first and second outer layers is composed of polymer material, or both layers are composed of polymer material. The polymer material includes but is not limited to polyethylene (PE), high density polyethylene (HDPE), polypropylene (PP), polyvinyl chloride (PVC), polyvinylidene chloride (PVDC), polyamide (PA), biaxially oriented polyamide (OPA), cyclo olefin copolymer (COC), polyurethane (PU) or their mixtures, for example, the mixture of COC and PE, and the mixture of COC and PVC.

In a further preferred embodiment, the first and second outer layers may be comprised of several sub-layers. For example, the first outer layer may contain a PVC layer and an OPA layer, the second outer layer may also contain a PVC layer and an OPA layer; but the PVC material of the first outer layer differs from the PVC material of the second outer layer by having different fillings. Although both of them are called PVC, their physical and chemical properties are significantly different, indicating that the first outer layer and the second outer layer are actually different materials. Another example is the first layer contains PP, the second outer layer contains OPA and PP layers. Thus the complex material is composed of PP/Al/OPA/PP. A third example is PVC/OPA/Al/PVC complex material.

From the perspective of protecting the pharmaceuticals from contamination of water vapor, light and other contaminants from the outside, and extending the shelf life of the pharmaceuticals, a preferred substrate material is PE/OPA/Al/OPA, wherein the first outer layer is OPA and the second outer layer is comprised of an OPA layer and a PE layer. This is because the PE material has good blocking ability, excellent transparency, no toxicity, good manufacturing adaptability and is recyclable. The aforesaid PE material can be water based PE or oil based PE.

Alternatively, from the perspective of enhancing the heat-sealing property of the material, COC can be used to significantly block water vapor exposure of tablets, which is especially important to oral disintegration preparation. Furthermore, COC is resistant to heat, acid and alkaline and has high strength. But COC is fragile and should be used in combination with other materials. In a preferred embodiment, the substrate material contains a first outer layer that is comprised of an OPA layer and a COC and PE mixture layer, and a second outer layer comprised of an OPA layer and a COC and PE complex layer. Namely, the structure of the substrate material is COC and PE mixture/OPA/Al/OPA/COC and PE complex. The meaning of "COC and PE mixture layer" (referred to as "COC+PE") is the material made by mixing COC and PE uniformly. The meaning of "COC and PE complex layer" (referred to as "COC/PE") is pressing a layer of COC and a layer of PE together to make a combined layer.

Additionally, from the perspective of avoiding warp in the manufacturing process so as to meet the technical requirements of the production, as well as reducing the cost, the preferred substrate material contains a first outer layer comprised of an OPA layer and a COC and PE mixture layer, and a second outer layer comprised of OPA. Therefore, the structure of the substrate material is COC+PE/OPA/Al/OPA.

Another aspect of this invention relates to the uses of the complex aluminum material for packaging products, especially products with blister packages. There are no special limitations to the packaged products. For example, they can be pharmaceuticals, cosmetics, nutritional supplements, food, seasonings and other desired compositions. Using the aforesaid complex aluminum material can effectively prevent the packages from warping and affecting the seal of the products in the package molding, heating, refrigeration and/or freezing process, and thus prevent contamination from water vapor, light and other contaminants from the outside and significantly increase the storage life of the products.

Binders can be added between each aforesaid layer to bind the complex materials together if necessary. Here, binders will be used when necessary and will not be separately mentioned in the following examples.

EXAMPLES

The following examples describe the invention with detailed embodiments. These examples are for the purpose of illustrating the invention only and not to limit the scope of the present invention.

Example 1

FIG. 1 is a structural diagram of the complex aluminum package material used in this example. This structural diagram shows that the structure of the complex material is: the top layer B is the water based PE layer, the layer beneath it is the OPA layer, the intermediate layer A is aluminum foil and the bottom layer C is the OPA layer.

Furthermore, of the substrate material used in this example, the thickness of layer B is 15 micrometers, the thickness of layer C is 25 micrometers and the thickness of the intermediate layer A is 60 micrometers.

The flexural rigidity of the materials is measured in accordance with the ASTM D790 standard of the American Society of Testing and Materials (ASTM) (the flexural rigidity of all the following materials is measured with the same method).

After analysis and testing, the flexural rigidity of the aforesaid complex material B is 4N, that of layer C, which is immediately next to layer B, is 40N, and that of the bottom layer C is also 40N.

Aluminum depressions are formed in the complex aluminum substrate material shown in FIG. 1 using blister molding equipment. A prepared pharmaceutical solution or suspension is added into the depressions with an electronic pipette. The pharmaceuticals and the substrate material are put into a liquid nitrogen tunnel at −80° C. for 7 minutes to freeze. In the foregoing technical process, the substrate material is impacted by the molding equipment. But the substrate material with a plurality of depressions remains flat without warp because the flexural rigidity of the first outer layer differs from that of the second outer layer by 21%. Subsequently, after the low temperature freeze in the liquid nitrogen tunnel, the aluminum material may warp a little because of the temperature change. But the warp is barely detectable unless closely observed and will not affect the solid tablets formed in the depressions.

Next, the frozen pharmaceuticals and the complex materials are moved to a freeze dryer and dried for 4.5 hours under the pressure of 0.2 mbar and the temperature of −20° C. Finally, the pharmaceuticals are sealed in the depressions using the lidding material and freeze-dried tablets are prepared.

Example 2

Figure 2:
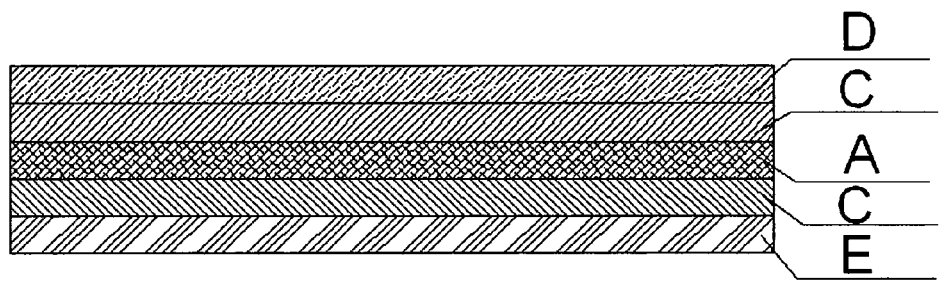
FIG. 2 is a structural diagram of a four-layer complex aluminum material used in another preferred embodiment of this invention. A stands for an aluminum foil layer, C stands for an OPA layer, D stands for a COC and PE mixture layer, and E stands for a COC and PE complex layer.

FIG. 2 is a structural diagram of the complex aluminum package material used in this example. This structural diagram shows that the structure of the complex material from top to bottom is: the COC and PE mixture layer (layer D), the OPA layer (layer C), aluminum foil (layer A), the OPA layer (layer C) and the COC and PE complex layer (layer E).

Of the substrate material used in this example, the thickness of layer D is 60 micrometer, the thickness of layer C is 25 micrometer, the thickness of the intermediate layer A is 60 micrometer and the thickness of layer E is 25 micrometers.

After analysis and testing, the flexural rigidity of the aforesaid layer D is 4N, that of the layer C is 15N, and that of the layer E is also 4N.

Aluminum depressions are formed in the complex aluminum substrate material shown in FIG. 2 using blister molding equipment. A prepared pharmaceutical solution or suspension is added into the depressions with an electronic pipette. The pharmaceuticals and the substrate material are put into a liquid nitrogen tunnel at −90° C. for 8 minutes to freeze. In the foregoing technical process, the substrate material is impacted by the molding equipment. But the substrate material with a plurality of depressions remains flat without warp because the flexural rigidity between the first outer layer and the second outer layer is the same. Subsequently, after the low temperature freeze in the liquid nitrogen tunnel, the aluminum material may warp a little because of the temperature change. But the warp is barely detectable unless closely observed and it will not affect the solid tablets formed in the depressions.

Next, the frozen pharmaceuticals and the complex materials are moved to a freeze dryer and dried for 4 hours under a pressure of 0.1 mbar and temperature of −10° C. Finally, the pharmaceuticals are sealed in the depressions using the lidding material and freeze-dried tablets are prepared.

Example 3

Figure 3:
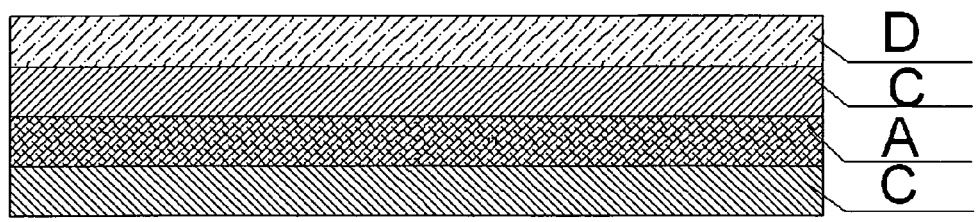
FIG. 3 is a structural diagram of a four-layer complex aluminum material used in another preferred embodiment of this invention. A stands for an aluminum foil layer, C stands for an OPA layer, and D stands for a COC and PE mixture layer.

FIG. 3 is a structural diagram of the complex aluminum package material used in this example. This structural diagram shows that the structure of the complex material is: the top layer D is the COC and PE mixture layer, the layer C beneath it is the OPA layer, the intermediate layer A is aluminum foil and the bottom layer C is the OPA layer.

Of the substrate material used in this example, the thickness of layer D is 25 micrometer, the thickness of layer C is 25 micrometers and the thickness of the intermediate layer A is 60 micrometers.

After analysis and testing, the flexural rigidity of the aforesaid complex materials D is 4N, that of the layer C, which is immediately next to layer B, is 15N, and that of the bottom layer C is also 15N.

Aluminum depressions are formed in the complex aluminum substrate material shown in FIG. 3 using blister molding equipment. A prepared pharmaceutical solution or suspension is added into the depressions with an electronic pipette. The pharmaceuticals and the substrate material are put into a liquid nitrogen tunnel at −100° C. for 5 minutes freeze. In the foregoing technical process, the substrate material is impacted by the molding equipment. But the substrate material with a plurality of depressions still remains flat without warp because the flexural rigidity of the first outer layer differs from that of the second outer layer by 21%. Subsequently, after the low-temperature freeze in the liquid nitrogen tunnel, the aluminum material may warp a little because of the temperature change. But the warp is barely detectable unless closely observed and it will not affect the solid tablets formed in the depressions.

Next, the frozen pharmaceuticals and the complex materials are moved to a freeze dryer and dried for 4 hours under the pressure of 0.1 mbar and the temperature of −20° C. Finally the pharmaceuticals are sealed in the depressions using the lidding material and freeze-dried tablets are prepared.

We claim:

1. A method for manufacturing a composition in blister packages, which comprises:
   (a) molding a complex aluminum substrate material with blister molding equipment, forming a plurality of depressions in said complex aluminum substrate material, wherein said complex aluminum substrate material comprises an intermediate aluminum layer, and first and second outer layers, wherein the first and second outer layers are composed of materials selected from polyethylene, polypropylene, polyvinyl chloride, polyvinylidene chloride, polyamide, cyclo olefin copolymer, polyurethane or their mixture, wherein material of the first outer layer differs from that of the second outer layer, and flexural rigidity of the first outer layer differs from that of the second outer layer by 0-30%;
   (b) filling a liquid composition into the plurality of depressions formed in step (a);
   (c) freezing said composition;
   (d) freeze-drying said composition;
   (e) attaching a lidding material to said package material to seal said composition,
   wherein, the first outer layer comprises an OPA layer and a layer of COC and PE mixture, and the material of the second outer layer is selected from polyethylene, polypropylene, polyvinyl chloride, polyvinylidene chloride, polyamide, cyclo olefin copolymer, polyurethane or their mixture.

2. The method of claim 1, wherein the flexural rigidity of the first outer layer differs from that of the second outer layer by 0-15%.

3. The method of claim 2, wherein the flexural rigidity of the first outer layer differs from that of the second outer layer by 0-5%.

4. The method of claim 3, wherein the flexural rigidity of the first outer layer and the second outer layer is the same.

5. The method of claim 1, wherein said first and second outer layers further include multiple sub-layers.

6. The method of claim 1, wherein the first outer layer comprises an OPA layer and a layer of the COC and PE mixture; the second outer layer comprises an OPA layer and a layer of the COC and PE complex and the structure of the substrate material is COC+PE/OPA/Al/OPA/COC/PE.

7. The method of claim 6, wherein the thickness of the OPA layer of said first outer layer is the same as that of the OPA layer of the second outer layer, and the thickness of the COC and PE mixture layer of said first outer layer is the same as that of the COC and PE complex layer of said second outer layer.

8. The method of claim 1, wherein said composition is selected from the group consisting of pharmaceuticals, cosmetics, nutritional supplements, food and seasonings.

9. The method of claim 8, wherein said composition is pharmaceuticals.

10. The method of claim 1, wherein said composition is oral disintegrating preparation.

11. The method of claim 1, wherein the second outer layer comprises an OPA layer and the structure of the substrate material is COC+PE/OPA/Al/OPA.

* * * * *